United States Patent [19]
Malchow

[11] Patent Number: 5,257,901
[45] Date of Patent: Nov. 2, 1993

[54] QUICK-PRIMING CENTRIFUGAL PUMP

[75] Inventor: Gregory L. Malchow, Oshkosh, Wis.

[73] Assignee: Whirlpool Corporation, Benton Harbor, Mich.

[21] Appl. No.: 908,823

[22] Filed: Jun. 24, 1992

Related U.S. Application Data

[63] Continuation of Ser. No. 635,287, Dec. 28, 1990, abandoned.

[51] Int. Cl.⁵ .............................................. F01D 25/24
[52] U.S. Cl. ................................. 415/182.1; 415/56.2; 415/206; 415/208.1
[58] Field of Search ............... 415/182.1, 206, 208.1, 415/56.1, 56.2

[56] References Cited

U.S. PATENT DOCUMENTS

| 2,000,480 | 5/1935 | Gorissen | 415/182.1 |
| 2,211,526 | 8/1940 | Storey | 415/206 |
| 2,291,760 | 8/1942 | Rupp | 103/113 |
| 3,421,446 | 1/1969 | Strscheletzly et al. | 415/182.1 |
| 3,489,340 | 1/1970 | Holzhausen | 230/127 |
| 3,735,782 | 5/1973 | Strscheletzly | 415/182.1 |
| 4,019,829 | 4/1977 | Knopfel et al. | 415/143 |
| 4,052,133 | 10/1977 | Yeater | 415/200 |
| 4,087,994 | 5/1978 | Goodlaxson | 68/23.7 |
| 4,157,834 | 6/1979 | Burdette | 277/13 |
| 4,459,117 | 7/1984 | Jordan | 415/206 |
| 4,596,510 | 6/1986 | Arneth et al. | 415/175 |
| 4,743,161 | 5/1988 | Fisher et al. | 415/53 R |
| 4,824,332 | 4/1989 | Perkins et al. | 417/315 |

FOREIGN PATENT DOCUMENTS

| 387935 | 1/1924 | Fed. Rep. of Germany | 415/182.1 |
| 224316 | 12/1968 | U.S.S.R. | 415/206 |
| 2190430 | 11/1987 | United Kingdom | 415/216.1 |

Primary Examiner—John T. Kwon
Attorney, Agent, or Firm—Baker & Daniels

[57] ABSTRACT

A quick priming centrifugal pump for use in automatic washers and the like wherein the size of the vortex which is formed in the pump and which inhibits priming, is reduced in volume, therefore permitting the pump to be a quick priming pump. The pump includes an extended pump impeller hub which reduces the axial length of the vortex which can be formed in the pump inlet. Additionally, a bevelled cut on the end of the inlet further reduces the axial length of the vortex. Lastly, a projecting rib formed on the inner surface of the inlet reduces the diameter of the vortex which may be formed.

5 Claims, 1 Drawing Sheet

QUICK-PRIMING CENTRIFUGAL PUMP

This is a continuation of application Ser. No. 07/635,289, filed Dec. 28, 1990, now abandoned.

BACKGROUND OF THE INVENTION

This application relates to centrifugal pumps and in particular to centrifugal pumps for pumping liquid in an automatic washer.

In particular this invention relates to a quick priming centrifugal pump which reduces or eliminates air or "suds" lock.

Automatic washers utilize pumps for draining the water out of the tub at the end of a washing cycle. The liquid solution of water and detergent, including soap suds, normally present in the tub is thus pumped to the drain. When the pump is first started, or when pumping soap suds near the end of a drain cycle when very little water remains in the tub, the rotating pump impeller will tend to create a vortex inside the inlet of the pump. The vortex is composed of a central pocket consisting primarily of suds or air, which pocket is located within a circulating layer of liquid which surrounds the central air pocket. When this condition occurs, the impeller, which is in communication with the air pocket, will unsuccessfully attempt to pump the air against the head of liquid present in the pump outlet. Pump flow will thereby be severely restricted. This condition is commonly known as "suds lock". If this condition occurs even to a small extent when the pump is first started, the pump priming time may be unacceptably long, which may cause the washing cycle to be unduly long or whereby, in washing machines with a fixed time washing cycle, all of the water may not be expelled or drained from the tub.

U.S. Pat. No. 4,087,994 discloses a centrifugal pump with means for precluding air lock wherein the impeller of the pump includes finger-like projections on each blade which extend radially outwardly from the impeller body into the outer annulus of the pumping chamber. These projections cut through the liquid which has been centrifuged to the outer annulus, thus causing a turbulence which draws a portion of the liquid into the body of the impeller for mixing with trapped air. This mixing action causes the air to be centrifuged with liquid and alleviates air lock in the pump. However, it should be noted that the vortex formed at the inlet of the pump is not reduced in size or eliminated.

SUMMARY OF THE INVENTION

The present invention overcomes the disadvantages of the above described prior art centrifugal pumps by providing an improved centrifugal pump therefor.

Applicant has discovered that it is possible to reduce the occurrence and severity of suds lock and to reduce the priming time of a pump by minimizing the size of the vortex which is formed in the pump inlet. By permitting only a small vortex to form, a smaller central air pocket is formed whereby more liquid is allowed to be in communication with the pump impeller. Accordingly, a greater volume of liquid may be pumped when a small vortex is present, whereby the pump priming time will be reduced while the condition of suds lock is avoided.

The pump according to the present invention reduces the potential volume of the vortex by reducing the potential axial length of the vortex and/or the potential diameter of the vortex by the use of an extended pump impeller hub and/or a bevelled cut on the end of the pump inlet and/or a projecting rib on the inner surface of the inlet.

The pump according to the present invention includes a housing having an inlet and an outlet. The inlet is generally tubular in shape. The pump also includes a rotatable impeller which is driven by means of a rotatable shaft. The impeller includes an extended impeller hub which extends axially toward the volume defined by the tubular inlet and therefore reduces the effective axial length of the pump inlet volume in which a vortex may form. Furthermore, a bevelled cut is provided on the end of the tubular inlet thus further reducing the effective axial length of the vortex. Lastly, a projecting rib is formed on the interior surface of the tubular inlet, which rib projects radially inwardly and thereby reduces the diameter of the vortex which can form.

An advantage of the present invention is that a centrifugal pump is provided for use in an automatic washing machine wherein the size of the vortex is minimized, thereby reducing the pump priming time and avoiding the condition of suds lock.

A further advantage of the present invention is that it provides a low cost, high quality, yet simple centrifugal pump which avoids the deleterious effects of suds lock.

The present invention, in one form thereof, comprises a quick priming centrifugal pump including a housing. The housing has an inlet and an outlet for fluid to be pumped by the pump. The inlet is generally tubular in shape and includes a bevelled end. An impeller is rotatably mounted in the housing. The impeller includes an extended hub which projects toward the inlet for limiting the axial dimension of a vortex which may be formed in the inlet when the pump is operating.

The present invention, in one form thereof, comprises a quick priming centrifugal pump for use in a washing machine. The pump includes a housing which has both an inlet and an outlet for fluid to be pumped by the pump. The inlet is generally tubular in shape and includes a bevelled end. An impeller is rotatably mounted in the housing. The impeller also includes means for projecting toward the inlet to reduce the effective axial length of the volume defined by the inlet to thereby limit the volume of a vortex which may be formed in the inlet when the pump is operating.

The present invention, in one form thereof, comprises a quick priming centrifugal pump for use in a washing machine. The pump comprises a housing. The housing has an inlet and an outlet for fluid to be pumped by the pump. The inlet is generally tubular in shape. An impeller is rotatably mounted in the housing, the impeller including a rotatable shaft for driving the impeller and a vane secured to the shaft. The impeller includes means for projecting toward the inlet to reduce the effective axial length of the volume defined by the inlet. Radially inwardly projecting means is also formed on the inner tubular surface of the inlet to inhibit the formation of a stable vortex in the inlet when the pump is operating.

It is therefore desired to provide a centrifugal pump wherein the formation of suds lock is reduced or inhibited.

It is a further object of the present invention to provide a quick priming centrifugal pump wherein the time for priming is reduced.

A still further object of the present invention is to provide a low cost, high quality yet simple centrifugal pump which is quick priming.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DESCRIPTION OF THE PREFERRED EMBODIMENT

Figure 1:
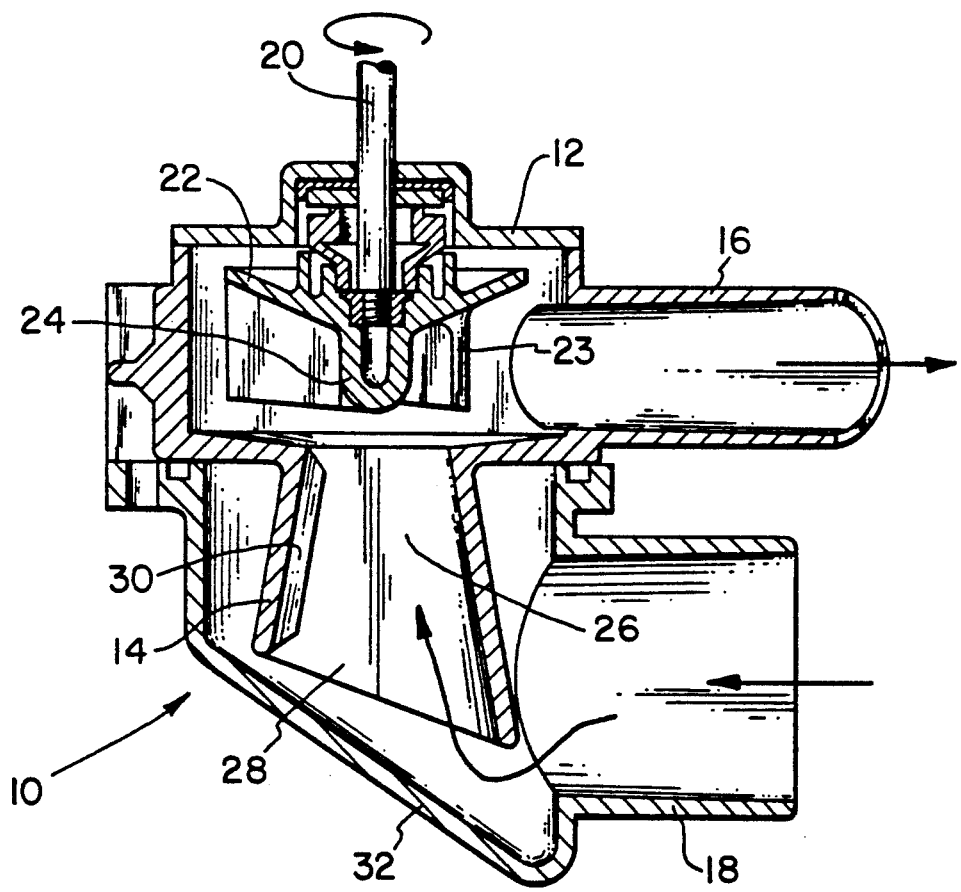
FIG. 1 is an elevational view in cross-section of the pump according to the present invention.

Referring to FIG. 1, there is shown a pump 10, in cross-section. The pump includes a housing 12 having an inlet 14 and an outlet 16. The inlet 14 is generally tubular in shape and has converging walls which converge inwardly toward an impeller 22. Impeller 22 is driven by means of a rotatable shaft 20 which is driven by suitable means (not shown).

A button trap 18 surrounds the inlet 14. Such a button trap is conventionally used for catching buttons and other small objects which settle out of the liquid wash water during the circulation thereof through pump 10 and thereby prevents such objects from damaging impeller 22 of pump 10.

Impeller 22 includes one or more vanes 23 as is conventional. When the impeller rotated it will draw liquid through button trap 18, as shown by the arrows, after which the liquid will enter inlet 14 and will be centrifugally forced by impeller 22 through outlet 16. Impeller 22 includes an extended impeller hub 24 which minimizes the size of the vortex which can be formed in the pump inlet 14. It can be seen that extended hub 24 extends towards inlet 14 and thereby projects into the area of the pump inlet which would normally be occupied by the core of the air and liquid vortex. By filling this area, the extended hub reduces the effective axial length of the pump inlet area in which a vortex may form, and displaces to some extent the air core which would normally be present at the center of the vortex.

Additionally, it can be seen that inlet 14 includes a bevelled end 28. The bevelled end further reduces the effective axial length of the vortex which may form in the pump inlet area and thereby further reduces the air core which would normally be present at the center of the vortex. It can be seen that button trap 18 also includes a wall 32 which is bevelled and shaped to conform to the shape of the bevelled inlet end of inlet 14. Lastly, a projecting rib 30 is secured to the inner wall of tubular inlet 14 and therefore projects radially inwardly into the volume wherein a vortex may form. The diameter of the vortex which may be formed is thereby reduced and turbulence is created to inhibit the formation of a stable vortex. The circulating outer layer of liquid of the vortex formed in prior art centrifugal pumps and which surrounds the central vortex air pocket, is broken up by the presence of axial rib 30.

In operation, when liquid is to be pumped by pump 10, liquid enters button trap 18, flows into the inlet 14 and is drawn further upwardly by means of the operation of rotating impeller 22. Since the volume of the vortex which would normally be formed at the inlet is reduced both axially and radially, any vortex which is formed is so small as to not unduly inhibit priming of the pump. Accordingly, the amount of air which is present in normal sudsy wash water, will not prevent the proper operation of the pump and the relatively quick priming thereof.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A quick priming centrifugal pump comprising:
   an upper housing having a pump inlet and a pump outlet for fluid to be pumped by said pump, said pump inlet being generally tubular in shape and defining an axis of fluid flow, said tubular pump inlet including a bevelled end;
   a lower housing at least partially surrounding said pump inlet, said lower housing including a lower housing inlet having an axis of fluid flow transverse to the axis of fluid flow of said pump inlet, said bevelled end facing away from said lower housing inlet;
   an impeller rotatably mounted in said upper housing, said impeller including an extended hub which projects toward said pump inlet for limiting the volume of a vortex which may be formed in said pump inlet when said pump is operating; and
   at least one rib means projecting radially and inwardly from an inner tubular surface of said pump inlet for inhibiting the formation of a vortex in said pump inlet during the operation of said pump.

2. A quick priming centrifugal pump for use in a washing machine, said pump comprising:
   an upper housing having a pump inlet and a pump outlet for fluid to be pumped by said pump, said pump inlet being generally tubular in shape and defining an axis of fluid flow, said tubular pump inlet including a bevelled end;
   a lower housing surrounding said pump inlet, said lower housing including a lower housing inlet having an axis of fluid flow transverse to the axis of fluid flow of said pump inlet, said bevelled end of said pump inlet facing away from said lower housing inlet;
   an impeller rotatably mounted in said upper housing, said impeller including a rotatable shaft for driving said impeller and a vane secured to said shaft, said impeller including means for projecting toward said pump inlet to reduce the volume of a vortex which may be formed in said pump inlet when said pump is operating; and
   radially inwardly projecting means formed on an inner tubular surface of said pump inlet for inhibiting the formation of a vortex in said pump inlet when said pump is operating.

3. The pump according to claim 2 wherein said projecting means comprises a rib which projects radially inwardly toward said pump inlet.

4. The pump according to claim 3 wherein said rib is disposed generally axially within said pump inlet.

5. The pump according to claim 2 wherein said means for projecting comprises an extended impeller hub.

* * * * *